United States Patent [19]

Kiddle

[11] Patent Number: Plant 6,955

[45] Date of Patent: Aug. 1, 1989

[54] APPLE TREE — GALAXY CULTIVAR

[75] Inventor: Kenneth W. Kiddle, Hawkes Bay, New Zealand

[73] Assignee: Stark Brothers Nurseries and Orchards Company, Louisiana, Mo.

[21] Appl. No.: 198,088

[22] Filed: May 24, 1988

[51] Int. Cl.[4] ..... A01H 5/00

[52] U.S. Cl. ..... Plt./34

[58] Field of Search ..... Plt. 34

*Primary Examiner*—Robert E. Bagwill

*Attorney, Agent, or Firm*—Burns, Doane, Swecker & Mathis

[57] ABSTRACT

A new and distinct variety of apple tree is provided which originated as a limb mutation of the Tenroy variety (U.S. Plant Pat. No. 4,121). The new variety produces attractive fruit having a solid cherry red coloration unlike that of the Tenroy variety. More specifically, the new variety possesses a solid intense cherry red coloration with often indistinct darker red overstriping. The red coloration of the new variety is present over the entire surface of the fruit and develops earlier than the coloration of the Tenroy variety.

2 Drawing Sheets

SUMMARY OF THE INVENTION

The new variety originated as a mutation of the Tenroy variety (U.S. Plant Pat. No. 4,121). The Tenroy variety is a mutation of the Kidd's D-8 variety (U.S. Plant Pat. No. 3,637). The mutation of the present invention was discovered by me during 1985 as a single spur on a seven year old tree of the Tenroy variety which produced fruit having a distinctive coloration. This attractive fruit coloration was recognized by me as being a commercially important improvement. The parent tree of the Tenroy variety was growing at the Huarangi Farm, Havelock North, Hawkes Bay, New Zealand. The fruit of the Tenroy variety is recognized to bear a red coloration which commonly assumes the configuration of stripes with a considerably lighter non-red ground coloration which shows between the stripes. On the contrary, the fruit of the new variety possesses a solid cherry red coloration which often indistinct darker red overstriping. Accordingly, the fruit exhibits a solid block red appearance over the entire fruit surface which was not typical of the Tenroy variety. The causation of the mutation is unknown.

Since its discovery in 1985, the new variety has been carefully preserved. Competing shoots and branches were removed and the original spur has developed into a large branch that now produces without reversion approximately 100 fruits which possess the distinctive coloration of the new variety. Buds of the new variety have been propagated at Department of Scientific and Research at Mt. Albert Research Centre, Auckland, New Zealand. Fruits possessing the distinctive coloration were produced during 1988 at that location. Also, grafts taken from the original branch have produced apples possessing the distinctive coloration for two seasons without any sign of reversion. Third generation trees of the new variety now produce 2 to 8 of the distinctive fruits on each tree. Accordingly, asexual propagation of the new variety beginning in March 1985 has well confirmed that the distinctive fruit coloration is stable and remains true to form after transmission through three generations.

It has been found that the characteristics of the new variety of apple tree of the present invention generally correspond to those of the Tenroy variety with two noteworthy exceptions. The entire surface of the fruit becomes colored with an attractive cherry red coloration and is not partially red colored as is the typical fruit of the Tenroy variety. Also, the color develops earlier on the fruit of the Tenroy cultivar which makes possible an earlier harvest.

The new variety also can be distinguished from other similar varieties which are non-patented in the United States and are incapable of developing fruit coloration in surface areas which are shaded.

Because of the excellent fruit coloring propensity of the new variety, it also offers potential for growing in areas where warmer climatic conditions commonly are encountered.

The new variety has been named the Galaxy variety.

BRIEF DESCRIPTION OF THE PHOTOGRAPHS

The accompanying photographs show typical specimens of the new variety as depicted in color as nearly true as it is reasonably possible to make the same in color illustrations of this character. The specimens were obtained at the Huarangi Farm, Havelock North, Hawkes Bay, New Zealand.

Figure 1:
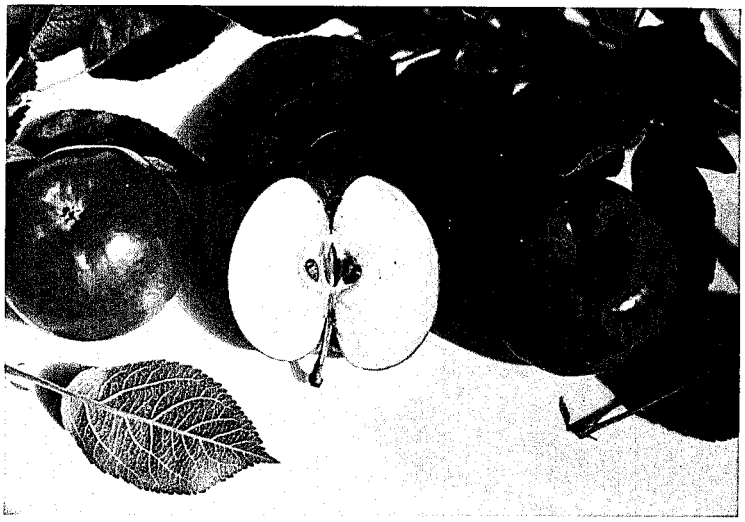
FIG. 1 illustrates specimens of the fully ripened fruit and foliage of the new Galaxy variety.
Figure 2:
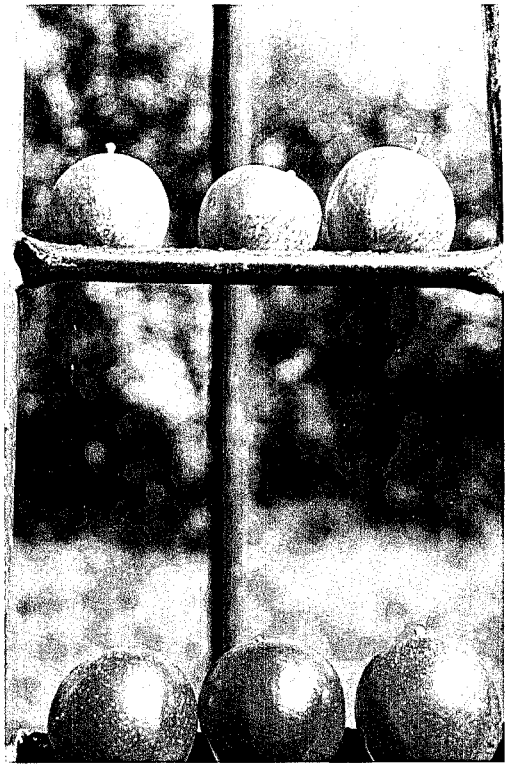
FIG. 2 illustrates commercially-ripe fruit specimens of the new Galaxy variety at the bottom and of the Tenroy variety at the top.
Figure 3:
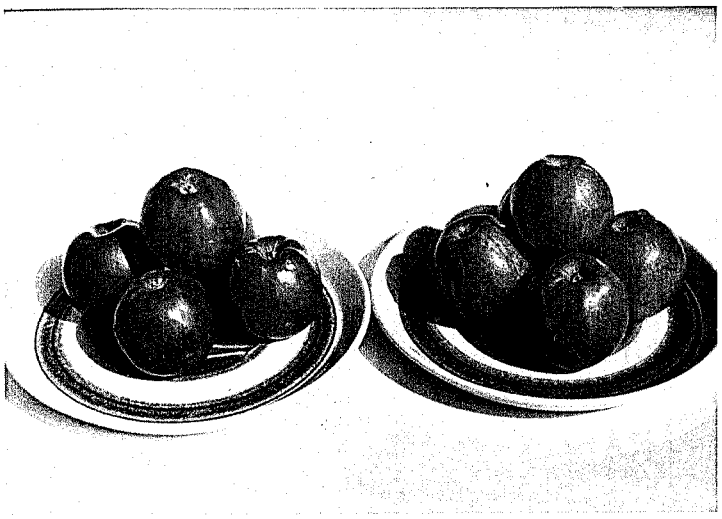
FIG. 3 illustrates fully ripened fruit specimens of the new Galaxy variety at the left and of the Tenroy variety at the right.

The darker striping on the fruit of the Galaxy variety tends to be partially obscured in some of the photographs by unavoidable light reflections due to reflective surfaces presented by the fruit.

DETAILED DESCRIPTION

The following is a detailed description of my new variety. The specimens described were grown at Huarangi Farm, Havelock North, Hawkes Bay, New Zealand.

The characteristics of the new variety are substantially the same as the Tenroy and Kidd's D-8 varieties except as indicated hereafter. For example, the new variety tends to exhibit the same vigor, blossom period, crop yield and disease resistance as the Tenroy and Kidd's D-8 varieties. The fruit of the new variety is the same in shape and size as these varieties and is equally variable in configuration.

The dates of the first and full bloom were Oct. 16, 1987, and Oct. 28, 1987, in New Zealand.

The dates of the first and last pickings were Feb. 12, 1988, and Feb. 29, 1988, in New Zealand.

The fruit coloration can be readily distinguished from that of other similar varieties. More specifically, the fruit of the Galaxy variety exhibits a solid and intense cherry red coloration with darker red overstriping often having indistinct borders. When one refers to *Methvens's Handbook of Colour* by A. Kornerup and J. H. Wanscher, Second Edition (1967) published by Methven & Co., London, the fruit of the Galaxy variety is colored cherry red (10B8) with darker striping of a madder red-blush tone (11B8). By comparison the Tenroy variety exhibits a turkey red (10C8) coloration with striping which only partially covers the surface of the fruit as illustrated. Some of the ground color of the Tenroy variety is not red. Unlike the Tenroy variety, the entire surface of the fruit of the Galaxy variety is colored red with the exception of the usual pale yellow dots which are present on both varieties. Red coloration develops well over the entire surface of the fruit of the Galaxy variety even if shade is encountered during its development. The general color effect of the new variety is one of a more intense red appearance.

The red coloration develops earlier on the Galaxy variety than on the Tenroy variety. Accordingly, it is possible to harvest the Galaxy fruits earlier than those of the Tenroy variety. For instance, it may be possible to harvest the Galaxy variety in only two or three pickings while the Tenroy and Kidd's D-8 varieties commonly require a greater number of pickings.

When blind taste tests are conducted with apples from mature trees, the taste and texture of the fruit of the new variety is found to be substantially identical to that of the Kidd's D-8 and Tenroy varieties.

I claim:

1. A new and distinct variety of apple tree, substantially as illustrated and described, which can be distinguished from the Tenroy variety by (1) the ability to form fruit which bears over its entire surface a cherry red coloration with an often indistinct darker red overstriping, and (2) the ability to produce fruit coloration on an earlier date.

* * * * *

TENROY VARIETY

GALAXY VARIETY

GALAXY VARIETY

TENROY VARIETY